(12) United States Patent
Mochizuki et al.

(10) Patent No.: US 9,650,582 B2
(45) Date of Patent: May 16, 2017

(54) BIODIESEL FUEL HYDROGENATION METHOD

(71) Applicant: NATIONAL INSTITUTE OF ADVANCED INDUSTRIAL SCIENCE AND TECHNOLOGY, Tokyo (JP)

(72) Inventors: Takehisa Mochizuki, Ibaraki (JP); Makoto Toba, Ibaraki (JP); Yuuji Yoshimura, Ibaraki (JP); Yohko Abe, Ibaraki (JP); Shih-Yuan Chen, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/123,740

(22) PCT Filed: Mar. 3, 2015

(86) PCT No.: PCT/JP2015/056237
§ 371 (c)(1),
(2) Date: Sep. 6, 2016

(87) PCT Pub. No.: WO2015/133487
PCT Pub. Date: Sep. 11, 2015

(65) Prior Publication Data
US 2017/0015918 A1    Jan. 19, 2017

(30) Foreign Application Priority Data
Mar. 3, 2014  (JP) .................. 2014-040590

(51) Int. Cl.
*C07C 51/36* (2006.01)
*C10L 1/02* (2006.01)
*C07C 67/283* (2006.01)

(52) U.S. Cl.
CPC ............ *C10L 1/026* (2013.01); *C07C 67/283* (2013.01); *C10L 2200/0476* (2013.01); *C10L 2270/026* (2013.01); *Y02E 50/13* (2013.01)

(58) Field of Classification Search
CPC .............................. C10L 1/026; C07C 67/283
(Continued)

(56) References Cited

U.S. PATENT DOCUMENTS

| 2007/0151143 A1 | 7/2007 | Li et al. |
| 2013/0055625 A1 | 3/2013 | Toba et al. |

FOREIGN PATENT DOCUMENTS

| EP | 1956070 A1 | 8/2008 |
| JP | 2002-020766 A | 1/2002 |

(Continued)

OTHER PUBLICATIONS

International Search Report in International Application No. PCT/JP2015/056237 dated May 19, 2015, 1 page.
(Continued)

*Primary Examiner* — Deborah D Carr
(74) *Attorney, Agent, or Firm* — Marshall, Gerstein & Borun LLP

(57) ABSTRACT

An object of the present invention is to provide a method for hydrogenating a biodiesel fuel for producing a biodiesel fuel having an excellent oxidation stability and cold flow property. The present invention serves to produce a biodiesel fuel excellent in oxidation stability, by hydrogenating a biodiesel fuel with oxygen present in the reaction system in the (Continued)

presence of a catalyst containing at least one type of noble metal selected from metals of Groups 8 to 10 in the periodic table.

3 Claims, 2 Drawing Sheets

(58) Field of Classification Search
USPC .......................................................... 554/141
See application file for complete search history.

(56) References Cited

FOREIGN PATENT DOCUMENTS

| JP | 2004-307608 | | 11/2004 | | |
|----|----|----|----|----|----|
| JP | 2007153937 | A | 6/2007 | | |
| JP | 2009-022938 | | 2/2009 | | |
| JP | 2009-057510 | | 3/2009 | | |
| JP | 2009522421 | A | 6/2009 | | |
| JP | 2011174028 | A | 9/2011 | | |
| JP | 5110607 | B2 | 12/2012 | | |
| TH | WO 2008105518 | A1 * | 9/2008 | ............ | B01J 23/755 |
| WO | WO-2008/105518 | A1 | 9/2008 | | |

OTHER PUBLICATIONS

International Preliminary Report on Patentability and Written Opinion in International Application No. PCT/JP2015/056237 dated Sep. 6, 2016, 5 pages.

* cited by examiner

BIODIESEL FUEL HYDROGENATION METHOD

TECHNICAL FIELD

The present invention relates to a method for hydrogenating a biodiesel fuel.

BACKGROUND ART

Biodiesel fuels composed of long chain fatty acid alkyl esters are produced from plant oils or animal fats, which are natural products, and thus, biodiesel fuels are increasingly introduced and becoming popular mainly in Europe and South East Asia, as environmentally friendly alternative fuels for light oil. European Standard EN 14214, Japanese standard JIS K2390, and American Standard ASTM D6751 are defined as standards for regulating the quality of biodiesel fuels in order to allow the safe use of biodiesel fuels as automotive fuels, and these quality standards must be met when biodiesel fuels are mixed with light oil and supplied to the market.

To improve the oxidation stability of biodiesel fuels, techniques of adding an antioxidant are known (Patent Documents 1 and 2). However, a large amount of antioxidant needs to be added in order to improve the oxidation stability of a biodiesel fuel with a high unsaturated fatty acid content, which leads to an increase in the fuel production cost. Further, the addition of an antioxidant to the biodiesel fuel does not solve the problem of sludge generation, and accordingly, further development of techniques which allow for improving the oxidation stability of biodiesel fuels is demanded.

The present inventors have therefore proposed hydrogenating catalysts capable of producing a biodiesel fuel having an extremely superior oxidation stability, by selectively hydrogenating polyunsaturated fatty acid alkyl esters containing two or more double bonds and having a poor oxidation stability, among the fatty acid alkyl esters contained in the biodiesel fuel, to monounsaturated fatty acid alkyl esters having a relatively excellent cold flow property and oxidation stability, under hydrogen pressure of atmospheric pressure (Patent Documents 3 and 4).

However, although the catalysts proposed by the present inventors have an excellent capability for selectively hydrogenating polyunsaturated fatty acid alkyl esters to monounsaturated fatty acid alkyl esters, biodiesel fuels derived from natural fats and oils contain various types of impurities such as sulfur compounds, nitrogen compounds and trace metals, and these impurities have caused a problem of poisoning the hydrogenating catalysts, thereby reducing their activity.

The removal of the impurities causing the inactivation of the catalyst is effective as a measure for solving the above mentioned problem, and a purification method utilizing an adsorbent is used for the removal (Patent Document 5). While the method utilizing an adsorbent has a high separation performance, it has an upper limit on the amount of adsorption, and thus, there are problems such as the necessity of using a large amount of adsorbent when the biodiesel fuel contains a large amount of impurities, and the dependency of the adsorption performance on the type of the adsorbent or the composition of the raw oil (crude biodiesel fuel), as well as the regeneration and disposal of the adsorbent after use.

Further, Patent Document 6 proposes a catalyst for hydrogenating fats and oils and a method for producing the catalyst. However, the techniques disclosed therein require that the hydrogenation be carried out under an extremely high pressure of 20 MPa, for example, and it is not clear as to whether these techniques are effective under low pressure conditions (1 MPa or less).

In addition, in order to carry out the hydrogenation of aromatic hydrocarbons contained in light oil using a noble metal catalyst, a method is disclosed in which 100 to 10,000 ppm of oxygen and/or an oxygen-containing organic compound is/are introduced into the reaction system along with hydrogen, to impart the catalyst with a resistance against impurities such as sulfur compounds and nitrogen compounds contained in light oil. However, the above mentioned technique requires that the hydrogenation be carried out under an extremely high pressure of 3.9 MPa, for example, and it is not clear as to whether it is effective under low pressure conditions (1 MPa or less), such as the conditions for carrying out the hydrogenation of a biodiesel fuel. Further, the above mentioned technique requires the addition of a heavy rare earth element(s) to the noble metal catalyst, in order to obtain the effect of adding oxygen and/or the oxygen-containing organic compound, and although it is effective in stabilizing the desulfurization activity, it is not effective in stabilizing the hydrogenation activity. Still further, the addition of oxygen and/or the oxygen-containing organic compound resulted in a decrease in the initial activities of both the desulfurization and the hydrogenation activities (Patent Document 7).

PRIOR ART DOCUMENTS

Patent Documents

Patent Document 1: JP 2009-57510 A
Patent Document 2: JP 2009-522421 A
Patent Document 3: JP 5110607 B
Patent Document 4: JP 2011-174028 A
Patent Document 5: JP 2004-307608 A
Patent Document 6: JP 2009-22938 A
Patent Document 7: JP 2002-20766 A

SUMMARY OF THE INVENTION

Problems to be Solved by the Invention

The present invention has been made in view of the current situation regarding conventional methods for hydrogenating biodiesel fuels. An object of the present invention is to provide a method for hydrogenating a biodiesel fuel for producing a biodiesel fuel having an excellent oxidation stability and cold flow property.

Means for Solving the Problems

The present inventors have made intensive studies to solve the above mentioned problems. As a result, they have discovered that, in the hydrogenation of a biodiesel fuel, when a biodiesel fuel containing oxygen is introduced in the presence of a catalyst containing a noble metal component to carry out a reaction, the catalyst exhibits a high hydrogenation activity and stability under hydrogen pressure conditions of 1.0 MPa or less, thereby completed the invention.

In other words, the present invention provides the following inventions.

[1] A method for hydrogenating a biodiesel fuel, the method comprising hydrogenating the biodiesel fuel in the presence of a catalyst containing at least one type of noble metal selected from metals of Groups 8 to 10 in the periodic table, wherein oxygen is allowed to be present in the reaction system.

[2] The method for hydrogenating a biodiesel fuel according to item [1], wherein the concentration of the oxygen in terms of oxygen molecules in the biodiesel fuel is from 150 to 3,500 ppm.

[3] The method for hydrogenating a biodiesel fuel according to item [1] or [2], wherein a gas containing oxygen is introduced into the reaction system.

[4] The method for hydrogenating a biodiesel fuel according to item [1] or [2], wherein the biodiesel fuel is forcibly oxidized in advance.

Effect of the Invention

The method for hydrogenating a biodiesel fuel according to the present invention is effective in improving the initial activity and stabilizing the activity of a hydrogenation catalyst for biodiesel fuel, and serves to produce a biodiesel fuel having an excellent oxidation stability. In addition, the method of the present invention is an extremely practical method which is useful in prolonging the life of the catalyst, since the method does not require the addition of a heavy rare earth element(s) to the catalyst, which has been essential in a conventional method; allows the catalyst to function under low pressure conditions of 1 MPa or less, which does not require a pressure-resistant or a high pressure facility; and allows for drastically reducing the deactivation of the hydrogenation activity.

EMBODIMENTS FOR CARRYING OUT THE INVENTION

Figure 1:
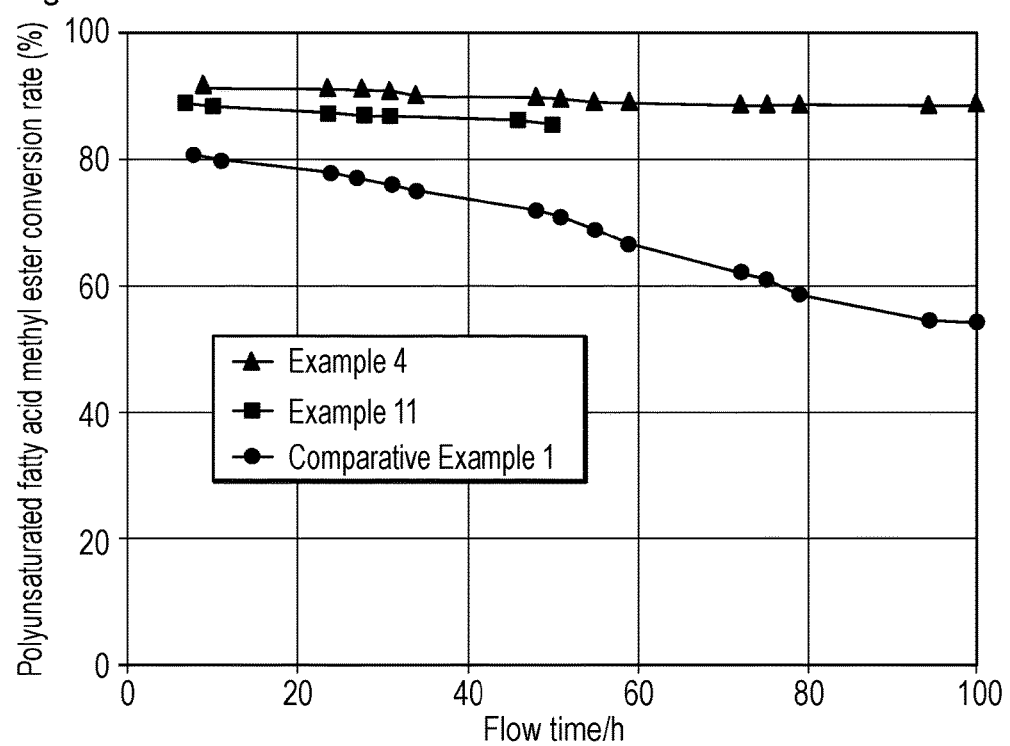
FIG. 1 is a graph illustrating the effect of adding oxygen on the hydrogenation reaction activity of Jatropha oil fatty acid methyl ester (FAME).

The present invention will now be described in detail.

The term biodiesel fuel as used in the present invention refers to one obtained by converting a natural fat or oil composed of a mixture comprising a fatty acid triglyceride as a major component and a diglyceride and/or a fatty acid monoglyceride as a secondary component(s), to fatty acid alkyl ester by transesterification with an alcohol.

The term "hydrogenation" as used in the present invention refers to a reaction in which hydrogen is added to an unsaturated bond. Particularly, in the present invention, it refers to a reaction in which hydrogen is added to a carbon-carbon double bond of unsaturated fatty acid methyl esters and unsaturated fatty acid monoglycerides, which are components of the biodiesel fuel.

The method for hydrogenating a biodiesel fuel in the present invention is not particularly limited. However, preferred is a method capable of partially hydrogenating polyunsaturated fatty acid methyl esters, which are components prone to oxidative degradation, to monounsaturated fatty acid methyl esters having a higher oxidation stability. This is because, when the unsaturated fatty acid methyl esters in a biodiesel fuel are fully hydrogenated to produce saturated fatty acid methyl esters, the pour point of the biodiesel fuel will be markedly increased, making the fuel unable to be used as a liquid fuel. Examples of the hydrogenation method as described above include methods disclosed in the above mentioned Patent Document 3 and Patent Document 4.

In order to carry out the hydrogenation of a biodiesel fuel, which hydrogenation is characteristic of the present invention, using the above mentioned method and while preventing a complete hydrogenation of unsaturated fatty acid methyl esters in the biodiesel fuel to saturated fatty acid methyl esters, it is preferred that the hydrogenation of the biodiesel fuel be carried out at a reaction temperature of from 80 to 130° C., and at a hydrogen pressure of from 0.2 to 0.7 MPa. If the reaction is carried out at a higher temperature or a high pressure than the above described ranges, it results in a marked concurrence of the complete hydrogenation to saturated fatty acid methyl esters. Further, if the reaction is carried out at a lower temperature or a lower pressure than the above described ranges, it results in a problem of insufficient hydrogenation.

When carrying out the hydrogenation, it is necessary that a hydrogenation catalyst be allowed to coexist in the reaction system. As the hydrogenation catalyst, a noble metal(s) selected from the metals of Groups 8 to 10 in the periodic table, such as palladium (Pd) and platinum (Pt) is/are used. The noble metal may be used singly, or a plurality of the noble metals can be used.

Further, it is preferred that the noble metal(s) be supported on a porous carrier. As the porous carrier, a porous inorganic oxide usually used as a catalyst for hydrogenating light oil or the like, a porous carbon material such as activated carbon, or a porous organic material containing an ion-exchange resin or the like can be used. Examples thereof include alumina, silica, titania, zirconia, silica-alumina, alumina-boria, alumina-titania, alumina-phosphorus, silica-titania, titania-zirconia and ultra-stable Y zeolite. In order to allow the noble metal(s) to be supported on a carrier, a general method for producing a hydrogenating catalyst can be used. Examples thereof include a method in which the noble metal is supported on a carrier by impregnating the carrier with an impregnation solution containing the noble metal by a known impregnation method; or a method in which a carrier precursor substance and the impregnation solution are kneaded, followed by molding, drying and calcining.

The present invention serves to improve the initial activity of the hydrogenation catalyst and to drastically reduce the deactivation of the hydrogenation activity of the hydrogenation catalyst, by allowing oxygen to be present in the reaction system while carrying out the hydrogenation of a biodiesel fuel. In cases where the hydrogenation of a biodiesel fuel is carried out with oxygen present in the reaction system, the type of reactor used is not particularly limited as long as it allows the catalyst to be in contact with the biodiesel fuel, hydrogen and oxygen supplied in a trace amount. Examples of the reactor which can be used include a fixed bed reactor in which a catalyst is fixed inside the reactor, a moving bed reactor in which a catalyst is allowed to move inside the reactor, a slurry reactor in which a catalyst is dispersed inside the reactor or the like.

In the present invention, examples of the method for allowing oxygen to be present in the reaction system include: a method in which a gas containing oxygen is introduced into the reaction system along with a biodiesel fuel, so as to achieve a predetermined oxygen concentration; and a method in which a biodiesel fuel itself is forcibly oxidized in advance to increase the oxygen concentration in the biodiesel fuel, followed by introducing the biodiesel fuel into the reaction system.

In cases where a gas containing oxygen is introduced into the reaction system along with the biodiesel fuel, it is possible to dissolve the gas containing oxygen into the biodiesel fuel as a feed stock to be supplied into the reaction system, or the gas containing oxygen may be supplied into the reaction system by a different means other than incorporating the gas into the biodiesel fuel as a feed stock, to allow contact with the catalyst.

Examples of the gas containing oxygen include oxygen gas, air gas, and the like.

The amount of oxygen to be present in the reaction system in terms of oxygen molecules is preferably 150 ppm or more and 3,500 ppm or less with respect to the amount of the biodiesel fuel. When the biodiesel fuel is forcibly oxidized in advance, the increased amount of oxygen in the biodiesel fuel as a result of the forced oxidation is defined as "the amount of oxygen to be present in the reaction system".

When the amount of oxygen in terms of oxygen molecules is less than 150 ppm, the effect of the invention may not be sufficiently obtained. When the amount of oxygen in terms of oxygen molecules is greater than 3,500 ppm, the oxidation of the hydrogenation catalyst may occur, and the hydrogenation activity may be reduced as the reaction time increases. The optimum amount of oxygen is dependent on the amount of the impurities contained in the biodiesel fuel, and the amount of oxygen to coexist in the reaction system needs to be increased as the amount of the impurities increases. It is particularly preferred that the amount of oxygen in terms of oxygen molecules be selected within the range of from 300 to 2,000 ppm, and more preferably within the range 400 to 1,500 ppm.

EXAMPLES

The invention will now be described based on Examples and Comparative Examples, but the invention is not limited thereto.

First, descriptions will be given regarding the methods for measuring the pour point, the oxidation stability, the peroxide value and the composition of fatty acids in a biodiesel fuel, and the definition of the deactivation rate, which were used in Examples.

(Measurement of Pour Point)

The measurement of the pour point was carried out using an auto pour point/cloud point tester (Model MPC-102A; manufactured by Tanaka Scientific Limited.), which is compliant with American Standard ASTM D6749.

(Measurement of Oxidation Stability)

The measurement of the oxidation stability was carried out according to the method defined in European standard EN 14112: 2003 (Rancimat method). The measurement was carried out by: introducing 3 g of sample in a measuring container; supplying clean air into the measuring container at 10 L/h while heating the container to 110° C.; collecting a volatile degradation product(s) in water, and then measuring the period of time (induction time) required to reach a bending point at which the electrical conductivity of the water in which the volatile degradation product was collected abruptly changes. An auto fat and oil stability tester (Rancimat 743; manufactured by Metrohm AG) was used for the measurement.

(Measurement of Peroxide Value)

The measurement of the peroxide value (POV) was carried out according to the acetic acid-isooctane method based on the standard fat and oil analysis method 2.5.2.1. An auto titration device (Titrando 809; manufactured by Metrohm AG) was used for the measurement.

(Measurement of Fatty Acid Composition in Catalytically Hydrogenated Biodiesel Fuel)

The composition of the fatty acids contained in the biodiesel fuel after the hydrogenation was measured. A gas chromatography (Model 6890N; manufactured by Agilent Technologies Inc.) was used for the measurement (analysis conditions: detector=FID; column=(88% cyanopropyl) allylpolysiloxane capillary column (Agilent HP-88, length×inner diameter×membrane thickness=100 m×250 μm×0.2 μm); temperature increase conditions=155° C., 20 min. →temperature increase at 2° C./min. →230° C., 2.5 min; carrier gas flow rate: 2.40 ml/min. (constant flow mode); and split ratio: 100:1).

(Definition of the Deactivation Rate)

Deactivation rate $(h^{-1})$={(amount of polyunsaturated FAME in raw oil–amount of polyunsaturated FAME 25 hours after reaction)/(amount of polyunsaturated FAME in raw oil)–(amount of polyunsaturated FAME in raw oil–amount of polyunsaturated FAME 50 hours after reaction)/(amount of polyunsaturated FAME in raw oil)}/(50h–25h)

As the fatty acid alkyl ester oils, methyl ester of Jatropha oil and methyl ester of palm oil were used. Jatropha oil methyl ester was obtained from Thailand. The fatty acid composition and the physical property value of the methyl ester oils are shown in Table 1. The FAME as used here stands for Fatty Acid Methyl Esters.

TABLE 1

| | Concentration of respective components (%) | |
|---|---|---|
| FAME components | Jatropha oil FAME | Palm oil FAME |
| Saturated FAME | Total 21.88% | Total 50.01% |
| C12:0 | 0.01 | 0.45 |
| C14:0 | 0.06 | 1.26 |
| C16:0 | 14.39 | 43.42 |
| C17:0 | 0.1 | 0.1 |
| C18:0 | 7.03 | 4.26 |
| C20:0 | 0.21 | 0.38 |
| C22:0 | 0.04 | 0.07 |
| C24:0 | 0.05 | 0.07 |
| Cis-monovalent unsaturated FAME | Total 42.49% | Total 40.18% |
| c-C16:1 | 0.79 | 0.19 |
| c-C18:1 | 41.61 | 39.84 |
| c-C20:1 | 0.09 | 0.16 |
| c-C22:1 | 0 | 0 |
| c-C24:1 | 9 | 0 |
| Trans-monovalent unsaturated FAME | Total 0.15% | |
| t-C16:1 | 0.08 | 0.30 |
| t C18:1 | 0.07 | 0.03 |
| t-C20:1 | 0 | 0.05 |
| t-C22:1 | 0 | 0.21 |
| t-C24:1 | 0 | 0 |
| Divalent unsaturated FAME | Total 33.68% | Total 9.14% |
| Trivalent unsaturated FAME | Total 0.18% | Total 0.03% |
| Rancimat induction time (h) | 1.3 | 20.7 |
| Peroxide value (meq/kg) | 21 | 2.1 |
| In terms of oxygen concentration (ppm) | 168 | 16.8 |
| Pour point (° C.) | 3 | 13 |

Example 1

(Preparation of Hydrogenation Catalyst)

An alumina carrier was impregnated with an aqueous solution of palladium tetraammine complex by an impregnation method, such that 0.1 g (palladium content: 0.5 wt %) of palladium in terms of metal was supported on 20 g of the alumina carrier, to obtain a palladium/alumina hydrogenation catalyst A in which palladium was supported only on the surface of the alumina carrier.

(Hydrogenation of Biodiesel Fuel)

A reaction tube was filled with the resulting catalyst A, and then reduction treatment was carried out at 300° C. for 3 hours (temperature increase rate; 5° C./min) in a hydrogen flow (atmospheric pressure, 0.1 L/min). Then pure oxygen gas as an oxygen source and Jatropha oil FAME were introduced into the reaction tube such that the amount of oxygen added with respect to the amount of Jatropha oil FAME was 190 ppm, to carry out the hydrogenation of the Jatropha oil FAME.

The evaluation of the hydrogenation activity was carried out using a fixed bed flow reactor (upflow mode), under conditions of: a catalyst amount of 0.20 g; a hydrogen partial pressure of 0.5 MPa; a reaction temperature of 100° C.; a weight hourly space velocity (WHSV) of 144 $h^{-1}$; and a $H_2$/Jatropha oil FAME ratio of 405 NL/L. The resulting liquid product was collected on a regular basis, and analyzed with the gas chromatography. The results of the hydrogenation reaction are shown in Table 2. The FAME collected 25 h to 25.5 h after the start of the reaction was used for the measurement of the pour point and the oxidation stability.

Example 2

Hydrogenation of Biodiesel Fuel

A reaction was carried out in the same manner as in Example 1, except that the amount of oxygen added was changed to 300 ppm. The results of the hydrogenation reaction are shown in Table 2.

Example 3

Hydrogenation of Biodiesel Fuel

A reaction was carried out in the same manner as in Example 1, except that the amount of oxygen added was changed to 390 ppm. The results of the hydrogenation reaction are shown in Table 2.

Example 4

Hydrogenation of Biodiesel Fuel

A reaction was carried out in the same manner as in Example 1, except that the amount of oxygen added was changed to 810 ppm. The results of the hydrogenation reaction are shown in Table 2.

Example 5

Hydrogenation of Biodiesel Fuel

A reaction was carried out in the same manner as in Example 1, except that the amount of oxygen added was changed to 1,500 ppm. The results of the hydrogenation reaction are shown in Table 2.

Example 6

Hydrogenation of Biodiesel Fuel

A reaction was carried out in the same manner as in Example 1, except that the amount of oxygen added was changed to 2,000 ppm. The results of the hydrogenation reaction are shown in Table 2.

Example 7

Hydrogenation of Biodiesel Fuel

A reaction was carried out in the same manner as in Example 1, except that the amount of oxygen added was changed to 3,200 ppm. The results of the hydrogenation reaction are shown in Table 2.

Example 8

Hydrogenation of Biodiesel Fuel

A reaction was carried out in the same manner as in Example 1, except that an air gas (oxygen:nitrogen=21%:79%) was used as the oxygen source, and the amount of oxygen added with respect to the amount of Jatropha oil FAME was changed to 810 ppm. The results of the hydrogenation reaction are shown in Table 2.

Comparative Example 1

Hydrogenation of Biodiesel Fuel

A reaction was carried out in the same manner as in Example 1, except that no oxygen was added. The results of the hydrogenation reaction are shown in Table 2.

TABLE 2

| | Hydrogenation deactivation rate ($\times 10^{-4}$ $h^{-1}$) | Pour point (° C.) | Oxidation stability Induction time (h) |
|---|---|---|---|
| Example 1 | 18.0 | 16 | 9.1 |
| Example 2 | 9.9 | 17 | 12.2 |
| Example 3 | 7.2 | 18 | 14.2 |
| Example 4 | 6.4 | 18 | 14.5 |
| Example 5 | 7.3 | 20 | 14.6 |
| Example 6 | 10.0 | 20 | 14.5 |
| Example 7 | 19.9 | 19 | 14.2 |
| Example 8 | 5.5 | 21 | 15.2 |
| Comparative Example 1 | 26.6 | 12 | 7.1 |

Example 9

(Preparation of Hydrogenation Catalyst)

An alumina carrier was impregnated with an aqueous solution of platinum tetraammine complex by an impregnation method, and 0.184 g of platinum in terms of metal was allowed to be supported on 20 g of the alumina carrier, such that an equimolar amount of platinum as the palladium supported on the catalyst A was supported on the alumina carrier, thereby obtaining a platinum/alumina hydrogenation catalyst B in which platinum was supported only on the surface of the alumina carrier.

(Hydrogenation of Biodiesel Fuel)

A reaction was carried out in the same manner as in Example 3, except for using the catalyst B. The results of the hydrogenation reaction are shown in Table 3.

Example 10

(Preparation of Hydrogenation Catalyst)

An alumina carrier was impregnated with an aqueous solution of palladium tetraammine complex and platinum tetraammine complex (palladium/platinum=4 mol/mol) by an impregnation method, such that 0.08 g of palladium in terms of metal and 0.037 g of platinum in terms of metal were supported on 20 g of the alumina carrier, to obtain a palladium-platinum/alumina hydrogenation catalyst C in which palladium and platinum were supported only on the surface of the alumina carrier.

(Hydrogenation of Biodiesel Fuel)

A reaction was carried out in the same manner as in Example 3, except for using the catalyst C. The results of the hydrogenation reaction are shown in Table 3.

TABLE 3

| | Hydrogenation deactivation rate ($\times 10^{-4}$ h$^{-1}$) | Pour point (° C.) 25 hours | Oxidation stability Induction time (hours) 25 hours |
|---|---|---|---|
| Example 9 | 6.0 | 15 | 11.5 |
| Example 10 | 5.4 | 18 | 10.2 |

Example 11

(Preparation Jatropha oil FAME with Increased POV)

A volume of 300 ml of Jatropha oil FAME (oxygen concentration: 168 ppm) was introduced into a 1,000 ml glass beaker, and the resultant was placed in an incubator controlled at 60° C., and left to stand for 24 hours, 100 hours to be stored. The POV value of the resulting FAME was 59 meq/kg (472 ppm in terms of oxygen), which amounted to an oxygen concentration increase of 304 ppm.

(Hydrogenation of Biodiesel Fuel)

A reaction was carried out in the same manner as in Comparative Example 1, except for using the above prepared Jatropha oil FAME with a POV of 59 (meq/kg). The results of the hydrogenation reaction are shown in Table 4.

Example 12

(Preparation Jatropha oil FAME with Increased POV)

A volume of 300 ml of Jatropha oil FAME (oxygen concentration: 168 ppm) was introduced into a 1000 ml glass beaker, and the resultant was placed in an incubator controlled at 60° C., and left to stand for 100 hours to be stored. The POV value of the resulting FAME was 121 meq/kg (947 ppm in terms of oxygen), which amounted to an oxygen concentration increase of 779 ppm.

(Hydrogenation of Biodiesel Fuel)

A reaction was carried out in the same manner as in Comparative Example 1, except for using the above prepared Jatropha oil FAME with a POV of 121 (meq/kg). The results of the hydrogenation reaction are shown in Table 4.

TABLE 4

| | Hydrogenation deactivation rate ($\times 10^{-4}$ h$^{-1}$) | Pour point (° C.) 25 hours | Oxidation stability Induction time (hours) 25 hours |
|---|---|---|---|
| Example 11 | 6.8 | 17 | 11.5 |
| Example 12 | 8.0 | 16 | 10.2 |

FIG. 1 is a graph illustrating the changes over time of the hydrogenation activity (polyunsaturated FAME conversion rate) in the reactions carried out in Example 4, Example 11 and Comparative Example 1.

As can be clearly seen from FIG. 1, in the reaction carried out in Comparative Example 1 (-●-) in which no oxygen was added, the hydrogenation activity was decreased over time, whereas in the reaction carried out in Example 4 (-▲-) in which oxygen gas was introduced, and in the reaction carried out in Example 11 (-■-) in which the biodiesel fuel was forcibly oxidized in advance to increase the oxygen concentration, the hydrogenation activity was stably maintained over time.

Figure 2:
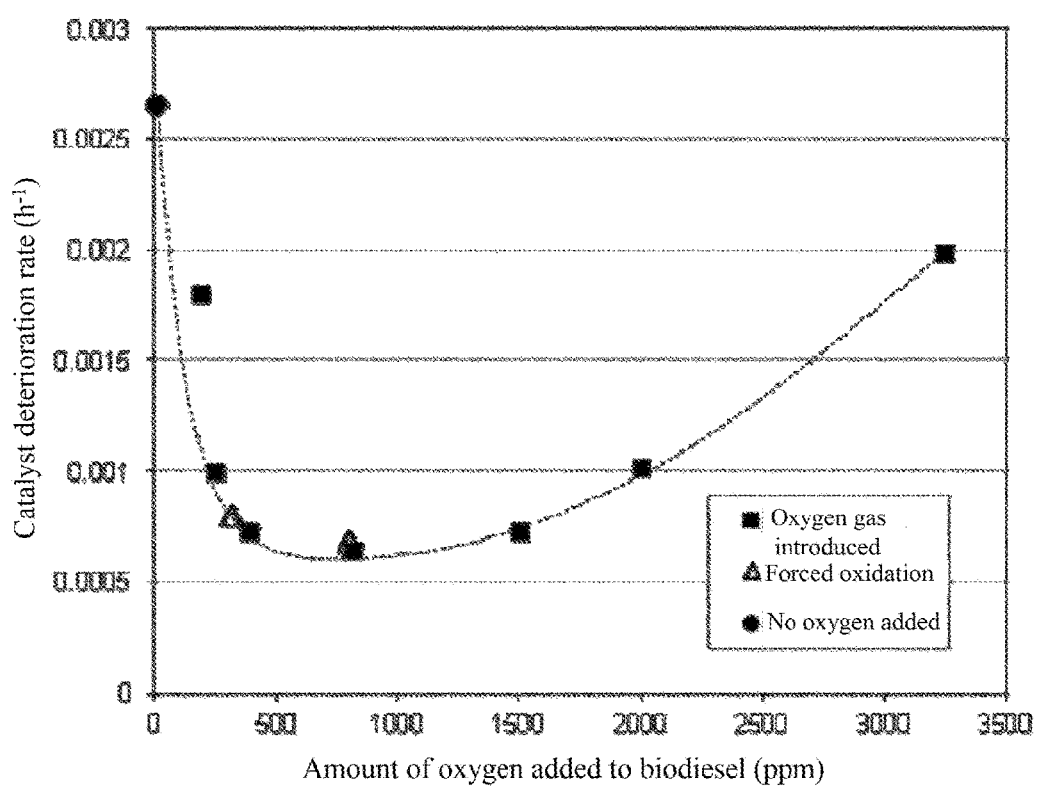
FIG. 2 is a graph illustrating the relationship between the hydrogenation deactivation rate of Jatropha oil FAME and the oxygen concentration in the reaction system.

FIG. 2 is a graph illustrating the relationship between the hydrogenation deactivation rate and the oxygen concentration in the reaction system in the reactions carried out in Examples 1 to 7, Examples 11 and 12, and Comparative Example 1. In FIG. 2, -■- represents the cases in which oxygen gas was introduced (Examples 1 to 7); -Δ- represents the cases in which the biodiesel fuel itself was forcibly oxidized in advance (Examples 11 and 12); and -●- represents the case in which no oxygen was added (Comparative Example 1).

As can be clearly seen from FIG. 2, the introduction of oxygen gas, preferably in an amount of from 150 to 3,500 ppm, and more preferably from 300 to 2,000 ppm, resulted in a decrease in the hydrogenation deactivation rate. This indicates that the introduction of oxygen gas was effective in stabilizing the hydrogenation activity. Further, it can be seen that the hydrogenation deactivation rate was also decreased when the biodiesel fuel was forcibly oxidized to increase the oxygen concentration. This indicates that the forced oxidation provides the same effect as the introduction of oxygen gas.

Example 13

Hydrogenation of Biodiesel Fuel

A reaction was carried out in the same manner as in Example 1, except that palm oil FAME was used as the raw oil FAME, and the amount of oxygen added was changed to 400 ppm. The results of the hydrogenation reaction are shown in Table 5.

Example 14

Hydrogenation of Biodiesel Fuel

A reaction was carried out in the same manner as in Example 13, except that the amount of oxygen added was changed to 810 ppm. The results of the hydrogenation reaction are shown in Table 5.

Example 15

Hydrogenation of Biodiesel Fuel

A reaction was carried out in the same manner as in Example 13, except that the amount of oxygen added was changed to 1,620 ppm. The results of the hydrogenation reaction are shown in Table 5.

Example 16

Hydrogenation of Biodiesel Fuel

A reaction was carried out in the same manner as in Example 13, except that the amount of oxygen added was changed to 2,430 ppm. The results of the hydrogenation reaction are shown in Table 5.

Comparative Example 2

Hydrogenation of Biodiesel Fuel

A reaction was carried out in the same manner as in Example 13, except that no oxygen was added. The results of the hydrogenation reaction are shown in Table 5.

TABLE 5

| | Hydrogenation deactivation rate ($\times 10^{-4}$ h$^{-1}$) | Pour point (° C.) | Oxidation stability Induction time (h) |
|---|---|---|---|
| Example 13 | 16.5 | 14 | >48 |
| Example 14 | 15.9 | 14 | >48 |
| Example 15 | 17.2 | 14 | >48 |
| Example 16 | 22.0 | 14 | >48 |
| Comparative Example 2 | 52.2 | 13 | 20.7 |

The invention claimed is:

1. A method for hydrogenating a biodiesel fuel, the method comprising hydrogenating a biodiesel fuel in the presence of a catalyst containing at least one type of noble metal selected from the group consisting of metals of Groups 8 to 10 in the periodic table, wherein oxygen is allowed to be present in the reaction system, wherein a concentration of the oxygen in terms of oxygen molecules in the biodiesel fuel is from 150 ppm to 3,500 ppm.

2. The method for hydrogenating a biodiesel fuel according to claim 1, comprising introducing a gas containing oxygen into the reaction system.

3. The method for hydrogenating a biodiesel fuel according to claim 1, comprising forcibly oxidizing the biodiesel fuel in advance.

* * * * *